(12) United States Patent
Andreella et al.

(10) Patent No.: US 8,618,284 B2
(45) Date of Patent: Dec. 31, 2013

(54) METHODS OF PREPARING POLYMORPHIC FORM A OF BAZEDOXIFENE ACETATE

(75) Inventors: Paolo Andreella, Verona (IT); Giuseppe Barreca, Lecco (IT); Francesco Tasinato, Padua (IT); Massimo Verzini, Caldiero (IT); Marco Demo, Verona (IT); Fabio Bassan, Padua (IT); Vincenzo Cannata, Borgonuovo di Sassomarconi (IT); Giorgio Soriato, Verona (IT); Roberto Brescello, Abano Terme (IT); Pietro Allegrini, Milan (IT); Livius Cotarca, Cervignano del Friuli (IT)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 13/453,574

(22) Filed: Apr. 23, 2012

(65) Prior Publication Data

US 2013/0018184 A1    Jan. 17, 2013

Related U.S. Application Data

(63) Continuation of application No. 12/369,104, filed on Feb. 11, 2009, now Pat. No. 8,183,367.

(60) Provisional application No. 61/027,634, filed on Feb. 11, 2008.

(51) Int. Cl.
*A61P 19/10* (2006.01)
*A61K 31/404* (2006.01)
*C07D 403/10* (2006.01)

(52) U.S. Cl.
USPC .......................................... 540/602

(58) Field of Classification Search
USPC .......................................... 540/602
See application file for complete search history.

(56) References Cited

U.S. PATENT DOCUMENTS

2005/0227965 A1    10/2005 Demerson et al.

OTHER PUBLICATIONS

Rhodes, "Drug Stability: Principles and Practices, 3rd Ed.", p. 215, Informa Health Care, London (Aug. 15, 2000).
Perosa, et al., "Mild Catalytic Multiphase Hydrogenolysis of Benzyl Ethers", Green Chemistry, 4:492-494 (2002).
Weissman, et al., "Recent Advances in Ether Dealkylation", Tetrahedron, 61(33):7833-7863 (2005).
International Search Report issued for PCT/US2009/033772, dated Apr. 29, 2009.

*Primary Examiner* — Brenda Coleman
(74) *Attorney, Agent, or Firm* — Stephanie J. Monaco (57) ABSTRACT

The present invention relates to methods of preparing polymorphic Form A of bazedoxifene acetate and polymorphic Form A prepared by such methods.

17 Claims, 9 Drawing Sheets

METHODS OF PREPARING POLYMORPHIC FORM A OF BAZEDOXIFENE ACETATE

CROSS REFERENCE TO RELATED APPLICATION

This application is a continuation under 35 U.S.C. 120 of U.S. patent application Ser. No. 12/369,104, filed Feb. 11, 2009, which claims the benefit of priority under 35 U.S.C. §119(e) to U.S. Patent Application Ser. No. 61/027,634 filed Feb. 11, 2008, both of which are hereby incorporated by reference in their entireties.

FIELD OF THE INVENTION

The present invention is directed to methods of preparing polymorphic Form A of bazedoxifene acetate; and polymorphic Form A of bazedoxifene acetate prepared by such methods.

BACKGROUND OF THE INVENTION

Bazedoxifene acetate has a chemical name of (1-[4-(2-azepan-1-yl-ethoxy)-benzyl]-2-(4-hydroxy-phenyl)-3-methyl-1H-indol-5-ol acetic acid) and has the chemical structure shown below:

Bazedoxifene acetate belongs to the class of drugs typically referred to as selective estrogen receptor modulators (SERMs). Consistent with its classification, bazedoxifene demonstrates affinity for estrogen receptors (ER) but shows tissue selective estrogenic effects. For example, bazedoxifene acetate demonstrates little or no stimulation of uterine response in preclinical models of uterine stimulation. Conversely, bazedoxifene acetate demonstrates an estrogen agonist-like effect in preventing bone loss and reducing cholesterol in an ovariectomized rat model of osteopenia. In an MCF-7 cell line (human breast cancer cell line), bazedoxifene acetate behaves as an estrogen antagonist. These data demonstrate that bazedoxifene acetate is estrogenic on bone and cardiovascular lipid parameters and antiestrogenic on uterine and mammary tissue and thus has the potential for treating a number of different disease or disease-like states in which the estrogen receptor is involved.

U.S. Pat. Nos. 5,998,402 and 6,479,535 report the preparation of bazedoxifene acetate and characterize the salt as having a melting point of 174°-178° C. The synthetic preparation of bazedoxifene acetate has also appeared in the general literature. See, for example, Miller et al., *J. Med. Chem.*, 2001, 44, 1654-1657, which reports the salt as a crystalline solid having a melting point of 170.5-172.5° C. Further description of the drug's biological activity has also appeared in the general literature (e.g., Miller, et al., *Drugs of the Future*, 2002, 27(2), 117-121).

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorphic form. In cases where two or more polymorph substances can be produced, it is desirable to have a method to make both polymorphs in pure form. In deciding which polymorph is preferable, the numerous properties of the polymorphs must be compared and the preferred polymorph chosen based on the many physical property variables. It is entirely possible that one polymorphic form can be preferable in some circumstances where certain aspects such as ease of preparation, stability, etc. are deemed to be critical. In other situations, a different polymorph may be preferred for greater solubility and/or superior pharmacokinetics.

Polymorphic Form A of bazedoxifene acetate is disclosed in US 2005/0227965 while polymorphic Form B of bazedoxifene acetate is disclosed in US 2005/0250762. Form A has higher solubility in both aqueous and organic solvent systems than Form B. This is particularly advantageous in formulations or doses where the solubility of the particular composition is of concern. For example, higher solubility can influence bioavailability, which can affect biological absorption and distribution of the drug, as well as can facilitate formulation in liquid carriers. However, Form A is the kinetic (or meta-stable) polymorph, while Form B is the thermodynamically more stable polymorph. Form A can easily convert to Form B upon contact with a solvent or solvent mixture (e.g., ethyl acetate and ethanol), which presents a challenge to the preparation of pure Form A that is substantially free of Form B.

Because polymorphic Form A of bazedoxifene acetate provides better bioavailability in some drug formulations, there is a need for a new and practical method that can reliably produce pure polymorphic Form A of bazedoxifene acetate. The methods of preparing polymorphic Form A of bazedoxifene acetate described herein help meet these and other needs. A method of preparing polymorphic Form A of bazedoxifene acetate is also disclosed in a commonly assigned and co-pending U.S. Patent Application Ser. No. 61/027,607, filed on Feb. 11, 2008.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

SUMMARY OF THE INVENTION

In one aspect, the present invention relates to a method of preparing polymorphic Form A of bazedoxifene acetate, the method comprising:

(a) contacting hexamethylenimino benzyloxyindole with hydrogen in a solvent comprising ethanol, and in the presence of a catalyst at elevated temperature to provide a first reaction mixture comprising bazedoxifene free base, wherein the first reaction mixture is substantially free from hexamethylenimino benzyloxyindole;

(b) treating said first reaction mixture with an antioxidant to provide a second reaction mixture;

(c) filtering said second reaction mixture to provide a solution comprising bazedoxifene free base; and (d) treating said solution with acetic acid to crystallize polymorphic Form A of bazedoxifene acetate.

In another aspect, the present invention relates to a method of enhancing the stability of polymorphic Form A of bazedoxifene acetate, the method comprising keeping said polymorphic Form A of bazedoxifene acetate in dry form and preventing the dry form from contacting with a solvent.

In yet another aspect, the present invention relates to a method of enhancing the stability of polymorphic Form A of bazedoxifene acetate, the method comprising keeping said polymorphic Form A of bazedoxifene acetate in dry form and preventing the dry form from contacting with the vapor of a solvent.

In a further aspect, the present invention relates to a polymorphic Form A of bazedoxifene acetate prepared according to the methods described herein.

Other features and advantages of the invention will be apparent from the detailed description, drawings, and from the claims.

DETAILED DESCRIPTION OF THE INVENTION

Polymorphic Form A of bazedoxifene acetate has higher solubility in both aqueous and organic solvent systems than polymorphic Form B of bazedoxifene acetate. As a result, Form A of bazedoxifene acetate provides better bioavailability in drug formulations. However, Form A is the kinetic (or meta-stable) polymorph while Form B is the thermodynamically more stable polymorph. Form A can easily convert to Form B upon contact with a solvent or solvent mixture (e.g., ethyl acetate and ethanol), which presents a challenge to the preparation of pure Form A that is substantially free of Form B. The present invention meets this challenge by providing methods of preparing pure Form A that is substantially free of Form B.

In one aspect, the present invention provides a method of preparing polymorphic Form A of bazedoxifene acetate, the method comprising:

(a) contacting hexamethylenimino benzyloxyindole with hydrogen in a solvent comprising ethanol, and in the presence of a catalyst at elevated temperature to provide a first reaction mixture comprising bazedoxifene free base, wherein the first reaction mixture is substantially free from hexamethylenimino benzyloxyindole;

(b) treating said first reaction mixture with an antioxidant to provide a second reaction mixture;

(c) filtering said second reaction mixture to provide a solution comprising bazedoxifene free base (i.e., bazedoxifene that is free of acid, e.g., acetic acid); and (d) treating said solution with acetic acid to crystallize polymorphic Form A of bazedoxifene acetate.

The term "substantially free" as used herein refers to a compound or a mixture that contains less than 10% of an undesired compound or impurity, preferably less than 5% of an undesired compound or impurity, and more preferably less than 1% of an undesired compound or impurity, e.g., less than 0.5% or less than 0.1% of an undesired compound or impurity. For example, "Compound A is substantially free of Compound B, or Mixture C is substantially free of Compound B" means that Compound A or Mixture C contains less than 10% of Compound B, preferably less than 5% of Compound B, and more preferably less than 1% of Compound B, e.g., less than 0.5% of Compound B or less than 0.1% of Compound B.

In certain embodiments, in step (a) of the method described herein, the solvent further comprises at least one solvent selected from the group consisting of ethyl acetate, acetone, cyclohexane and methanol, for example, ethanol-ethyl acetate, ethanol-acetone-cyclohexane, ethanol-methanol-cyclohexane, and so forth. In one embodiment, the solvent comprises ethanol and ethyl acetate.

In certain embodiments, step (a) of the method described herein is completed in less than about 10 hours. In certain other embodiments, step (a) is completed in less than about 6 hours. In further embodiments, step (a) is completed in less than about 4 hours, for example, in less than about 3 hours or about 2 hours.

In certain embodiments, in step (a) of the method described herein, the catalyst is a Pd/C catalyst. In one embodiment, the Pd/C catalyst used is in an amount less than about 10 mmol per mol of hexamethylenimino benzyloxyindole used. In another embodiment, the Pd/C catalyst used is in an amount less than about 6 mmol per mol of hexamethylenimino benzyloxyindole used.

In a further embodiment, the Pd/C catalyst has a total surface area (B.E.T) of more than about 1100 $m^2/g$. In one embodiment, the Pd/C catalyst has a total surface area (B.E.T) of more than about 1500 $m^2/g$. B.E.T. refers to Brunauer-Emmett-Teller and is a surface area measurement technique applied to large surface area 1-20 $m^2/g$ materials and based on adsorbed gas (e.g. $N_2$ at low temperature) as a function of pressure (monolayer coverage). See, e.g., G. A. Somorjai, *Principles of Surface Chemistry*, Prentice-Hall, Englewood Cliffs, N.J., 1972, p. 216.

In one embodiment, the Pd/C catalyst is non-reduced Pd on moist carbon and wherein the Pd/C catalyst is Engelhard 5% Pd on Carbon Powder DeLink code 5398. In another embodiment, the Pd/C catalyst is Engelhard 5% Pd on Carbon Powder catalyst code 5016. Both catalysts can be purchased from Engelhard Corporation, Iselin, N.J.

The two catalysts present very different physical-chemical characteristics. Table 1 below shows the principal characteristics of the two catalysts.

TABLE 1

| CATALYST: | 5% Pd on Carbon Power | 5% Pd on Carbon Power DeLink |
|---|---|---|
| CODE | 5016 | 5398 |
| Total Surface Area (B.E.T.) m²/g | 1100 | 1500 |
| Particle Size Distribution (Laser) | 10% < 5 microns | 10% < 6 microns |
| | 50% < 18 microns | 50% < 38 microns |
| | 90% < 96 microns | 90% < 75 microns |
| Active Metal | Palladium | Palladium |
| Active Metal Content | 5% on dry basis | 5% on dry basis |
| Metal Distribution | Uniform | Eggshell |
| Type | Reduced/Moist | Unreduced/Moist |

In certain embodiments, step (a) of the method described herein is carried out at a temperature of about 30° C. or higher (up to about 78° C., e.g., about 75° C., about 70° C., about 65° C., about 60° C., about 55° C., about 50° C., about 45° C., about 40° C., or about 35° C.). In certain other embodiments, step (a) is carried out at a temperature of about 40° C. or higher (up to about 78° C., e.g., about 75° C., about 70° C., about 65° C., about 60° C., about 55° C., about 50° C., or about 45° C.). In yet other embodiments, step (a) is carried out at a temperature between about 30° C. to about 50° C. In yet other embodiments, step (a) is carried out at a temperature between about 40° C. to about 50° C. In another embodiment, step (a) is carried out at a temperature of about 50° C.

In certain embodiments, in step (b) of the method described herein, said antioxidant is selected from ascorbic acid, sodium ascorbate, ascorbyl palmitate, citric acid, propyl gallate, alpha Tocopherol (vitamin E), vitamin E TPGS, vitamin E acetate, butylated hydroxytoluene, butylated hydroxyanisole and mixtures thereof. In another embodiment, said antioxidant is ascorbic acid.

In certain embodiments, step (d) of the method described herein is facilitated by seeding with polymorphic Form A of bazedoxifene acetate. In certain other embodiments, step (d) is carried out at a temperature of about 40° C. or lower (as low as 0° C., e.g., 35° C.; 30° C., 25° C., 20° C., 15° C., 10° C., or 5° C.). In yet other embodiments, step (d) is carried out at a temperature of about 30° C. or lower (as low as 0° C., e.g., 25° C., 20° C., 15° C., 10° C., or 5° C.). In yet other embodiments, step (d) is carried out at a temperature ranging from about 0° C. to about 40° C. In yet other embodiments, step (d) is carried out at a temperature ranging from about 0° C. to about 30° C. In certain embodiments, step (d) is carried out at a temperature ranging from about 20° C. to about 35° C. In certain other embodiments, step (d) is carried out at a temperature ranging from about 25° C. to about 30° C. In yet other embodiments, step (d) is carried out at a temperature ranging from about 28° C. to about 30° C.

In certain embodiments, steps (a) through (d) of the method described herein are conducted under inert atmosphere. Non-limiting examples of inert atmosphere include nitrogen, argon, and so forth.

In certain embodiments, in step (d) of the method described herein, said polymorphic Form A of bazedoxifene acetate is more than 99% w/w pure, for example, more than 99.9% w/w pure. In certain other embodiments, in step (d) of the method described herein, said polymorphic Form A of bazedoxifene acetate contains less than 1% w/w of Form B, for example, less than 0.1% w/w Form B.

In another aspect, the present invention provides a method of preparing polymorphic Form A of bazedoxifene acetate, the method comprising:

(a) contacting hexamethylenimino benzyloxyindole with hydrogen in a solvent comprising ethanol, and in the presence of a catalyst at elevated temperature to provide a first reaction mixture comprising bazedoxifene free base, wherein the first reaction mixture is substantially free from hexamethylenimino benzyloxyindole;

(b) treating said first reaction mixture with an antioxidant to provide a second reaction mixture;

(c) filtering said second reaction mixture to provide a solution comprising bazedoxifene free base;

(d) treating said solution with acetic acid to crystallize polymorphic Form A of bazedoxifene acetate; and (e) isolating polymorphic Form A of bazedoxifene acetate by filtration, washing and drying.

In certain embodiments, in step (e) of the method described herein, said drying is conducted in an agitated filter dryer. An agitated filter dryer is useful in separating solids from liquid in a single vessel. Once the dryer is charged with slurry, pressure is either applied from the top of the filter dryer using a gas, such as nitrogen, or a vacuum is pulled from beneath the filter media, thereby forcing or pulling liquid through the cloth or mesh to generate a cake. Low pressures are generally used (e.g., 1 bar) to keep the cake from becoming so compressed that the crystals fuse together. The liquid exits at the bottom of the vessel. While the crystals are collecting on the filter media, the smooth edge of the agitator acts to smooth the surface of the cake so there are no crevices. The other edge of the agitator, which can rotate in both directions, might have teeth for digging into the cake to help break it up and remove it from the filter media. The cake might be broken up and washed several times to remove all trace solvents or impurities. Heat may be applied to dryer to speed up the drying process.

The stirring frequency, instantaneous duration, total stirring duration and drying duration of the dryer may vary depending on, inter alia, the load of the product to be dried. In one embodiment, the stirring frequency is about 120 min., the instantaneous duration is about 2 min., the total stirring duration is about 18 min. and the drying duration is about 18 hours. In another embodiment, the stirring frequency is about 30 min., the instantaneous duration is about 1 min., the total stirring duration is about 38 min. and the drying duration is about 19 hours. In yet another embodiment, the stirring frequency is about 60 min., the instantaneous duration is about 1 min., the total stirring duration is about 18 min. and the drying duration is about 18 hours. In a further embodiment, the wet product is left at low temperature (e.g., about 0° C.) under nitrogen flow without stirring for a short period of time (e.g., about 1 hour) to reduce the product humidity level before the beginning of the drying process.

In certain other embodiments, in step (e) of the method described herein, said drying is conducted in a tumble dryer. The drying can be conducted in a tumble dryer under nitrogen, and/or vacuum conditions. The tumble dryer can be purchased from a variety vendors, for example, Italvacuum CRIOX in Italy.

In a further aspect, the present invention is directed to a method of enhancing the stability of polymorphic Form A of bazedoxifene acetate. The method includes keeping said polymorphic Form A of bazedoxifene acetate in dry form and preventing the dry form from contacting with a solvent. In one embodiment, the solvent can totally or partially dissolve said polymorphic Form A of bazedoxifene acetate.

In another aspect, the present invention is directed to a method of enhancing the stability of polymorphic Form A of bazedoxifene acetate. The method includes keeping the polymorphic Form A of bazedoxifene acetate in dry form and preventing the dry form from contacting with a solvent and keeping the polymorphic Form A of bazedoxifene acetate at a temperature below 25° C. or lower (as low as about −196 C, e.g., about 20° C., about 15° C., about 10° C., about 5° C., about 0° C., about −5° C., about −10° C., about −20° C., about −30° C., about −40° C., about −50° C., about −60° C., about −70° C., or about −80° C.), for example, at a temperature from about 0° C. to about 25° C.

In yet another aspect, the present invention is directed to method of enhancing the stability of polymorphic Form A of bazedoxifene acetate. The method includes keeping the polymorphic Form A of bazedoxifene acetate in dry form and preventing the dry form from contacting with the vapor of a solvent. In one embodiment, the solvent can totally or partially dissolve the polymorphic Form A of bazedoxifene acetate. Applicants have surprisingly found that Form A can partially transform into Form B in the presence of the vapor of a solvent such as ethanol.

In yet another aspect, the present invention is directed to a method of enhancing the stability of polymorphic Form A of bazedoxifene acetate. The method includes keeping the polymorphic Form A of bazedoxifene acetate in dry form and preventing the dry form from contacting with the vapor of a solvent and keeping the polymorphic Form A of bazedoxifene acetate at a temperature below 25° C. or lower (as low as about −196° C., e.g., about 20° C., about 15° C., about 10° C., about 5° C., about 0° C., about −5° C., about −10° C., about −20° C., about −30° C., about −40° C., about −50° C., about −60° C., about −70° C., or about −80° C.), for example, at a temperature from about 0° C. to about 25° C.

In one aspect, the present invention is directed to polymorphic Form A of bazedoxifene acetate prepared according to the methods described herein. In certain embodiments, the polymorphic Form A of bazedoxifene acetate prepared according to such methods is more than 99% w/w pure, for example, more than 99.5% w/w or more than 99.9% w/w pure. In certain other embodiments, the polymorphic Form A of bazedoxifene acetate contains less than 1% w/w of Form B, for example, less than 0.5% w/w or 0.1% w/w Form B. Throughout the application, the purity of Form A of bazedoxifene acetate refers to polymorphic purity.

The invention is further illustrated by the following examples. The examples are provided for illustrative purposes only. They are not to be construed as limiting the scope or content of the invention in any way.

EXAMPLES

Example 1

Infrared (IR) Analysis of Polymorphic Form A and Form B of Bazedoxifene Acetate

The solid state of both polymorphic Form A and Form B of Bazedoxifene Acetate has a characteristic Infrared (IR) spectrum. The transformation from Form A to Form B can be followed "on-line" by FT-IR/ATR and FBRM technology (Lasentec probe). The "IR on-line" experiments can be carried out using the system React-IR 4000 in the configuration that uses the probe with diamond sensor ATR (Dicomp). The "size-distribution on line" experiments are executed by using the system Lasentec FBRM equipped with D600R probe.

IR measures are carried out opportunely placing a few mg of the powder of the sample on the diamond sensor ATR of the probe. The inquired spectral interval is 4000-650 cm-1 with 4 cm$^{-1}$ resolution (128 scans for every collected spectrum). Some experiments are executed creating an ethanol vapor atmosphere around the ATR sensor avoiding the direct contact between the liquid solvent and the powder of bazedoxifene acetate.

Figure 1:
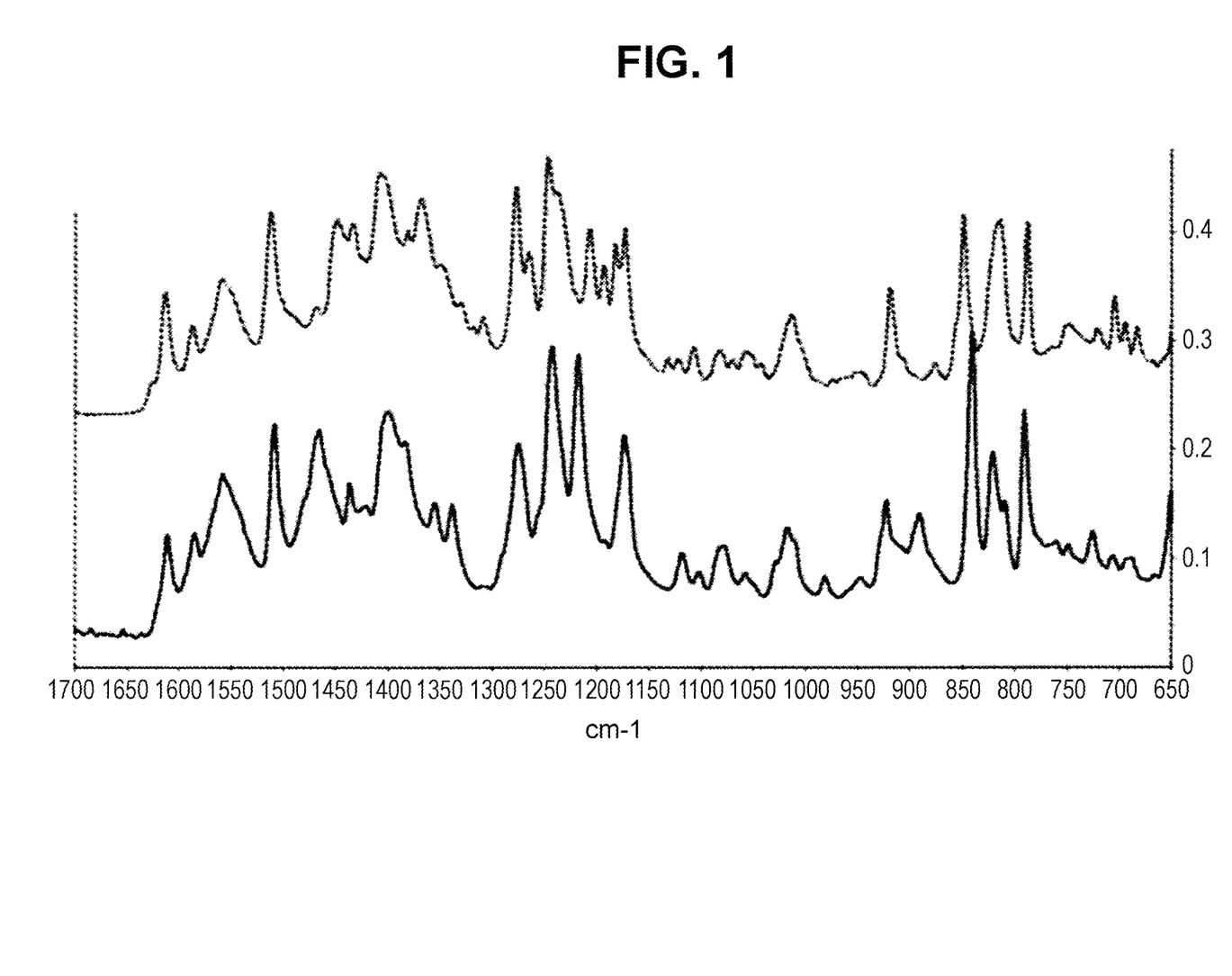
FIG. 1 shows an overlay of IR spectra of polymorphic Form A and Form B of bazedoxifene acetate (the bottom portion of FIG. 1 corresponds to Form A and the top portion corresponds to Form B).

Some characteristic absorption peaks of the polymorphic Form A and Form B of bazedoxifene acetate are shown in Table 2. FIG. 1 shows an overlay of IR spectra of polymorphic Form A and Form B of bazedoxifene acetate. The bottom portion of FIG. 1 is the IR spectrum for Form A while the top portion of FIG. 1 is the IR spectrum for Form B.

TABLE 2

| | IR Wavelength number (cm$^{-1}$) | | | |
|---|---|---|---|---|
| Form A | 841 | 1242 | 1356 | 1466 |
| Form B | 849 | 1207 | 1368 | 1449 |

Example 2

Figure 2:
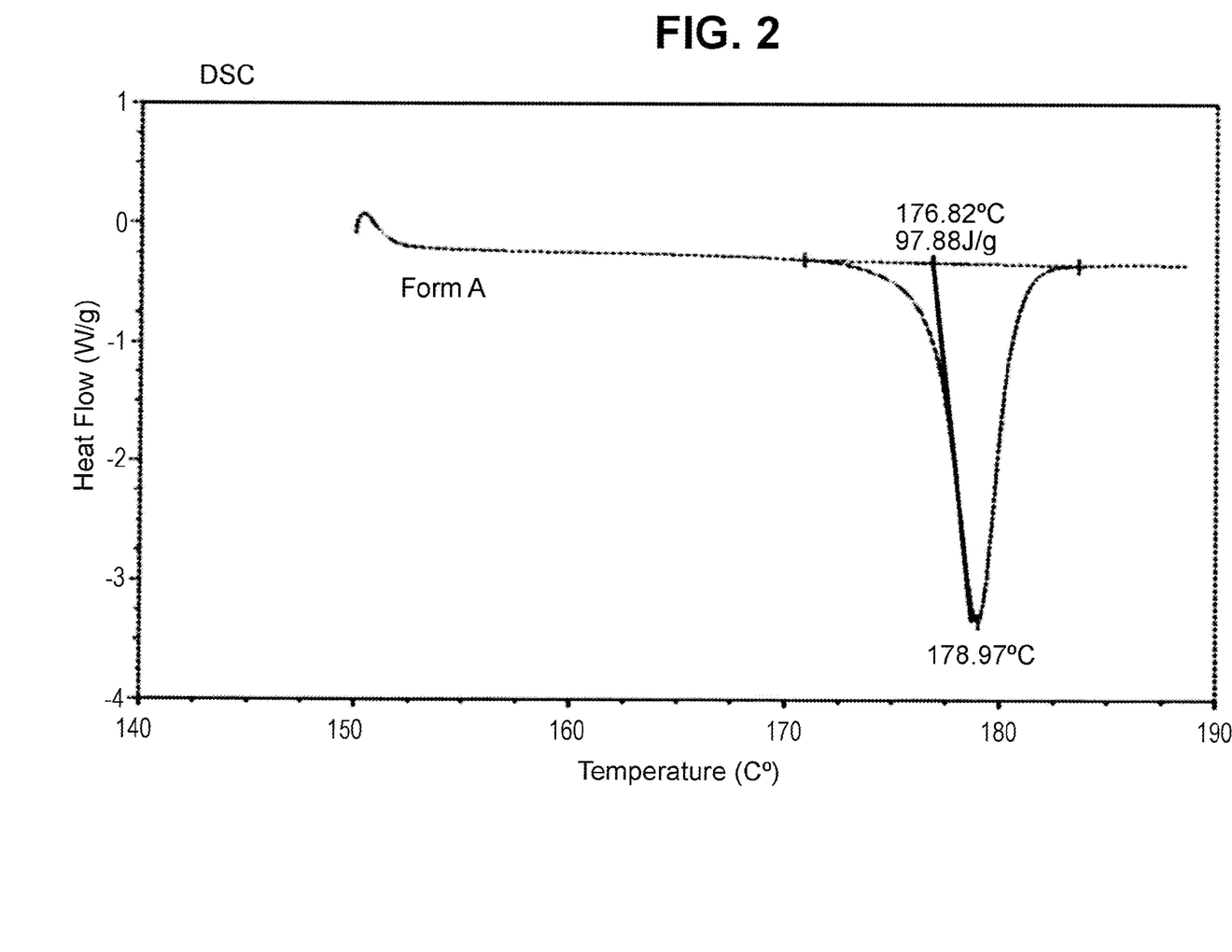
FIG. 2 shows a DSC thermogram for polymorphic Form A of bazedoxifene acetate.
Figure 3:
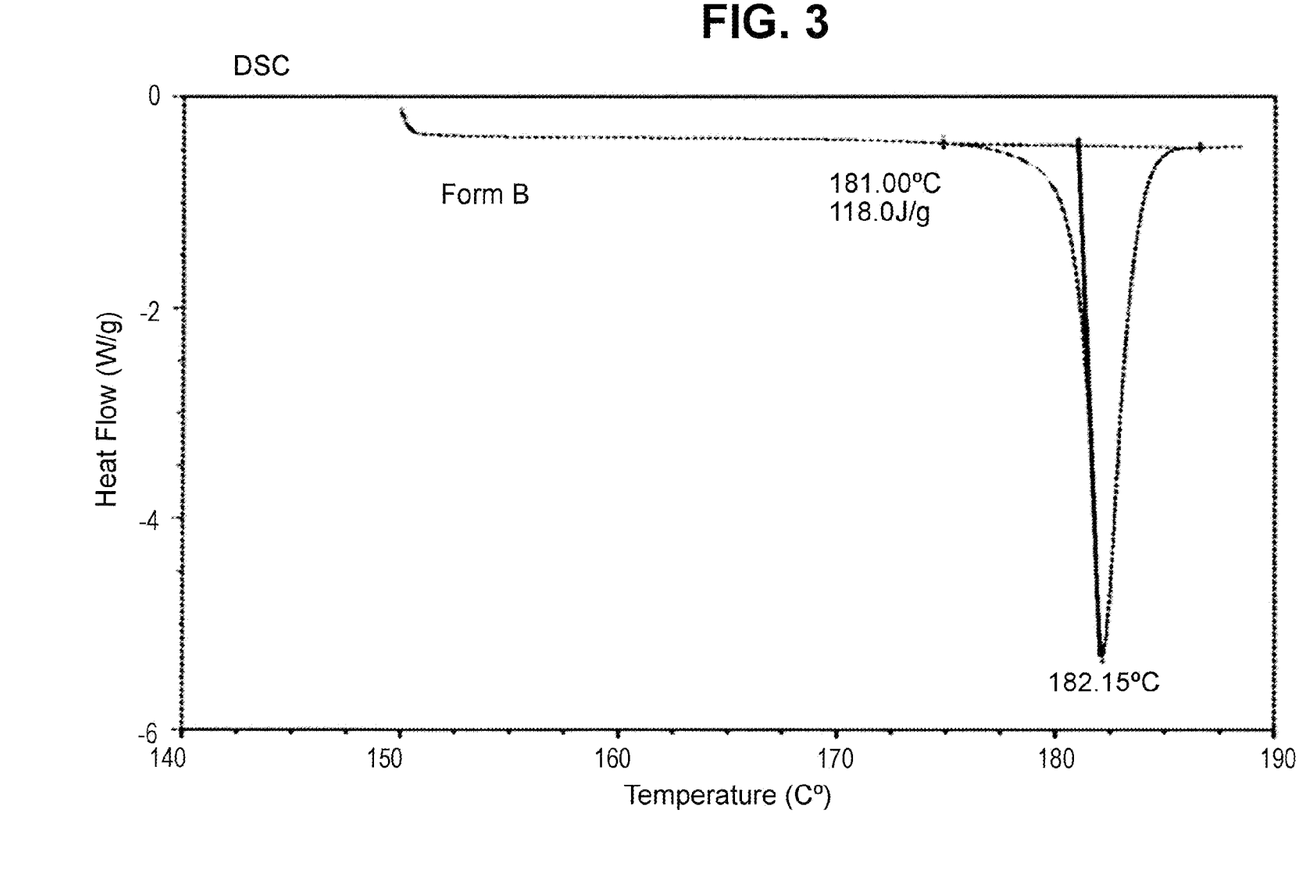
FIG. 3 shows a DSC thermogram for polymorphic Form B of bazedoxifene acetate.
Figure 4:
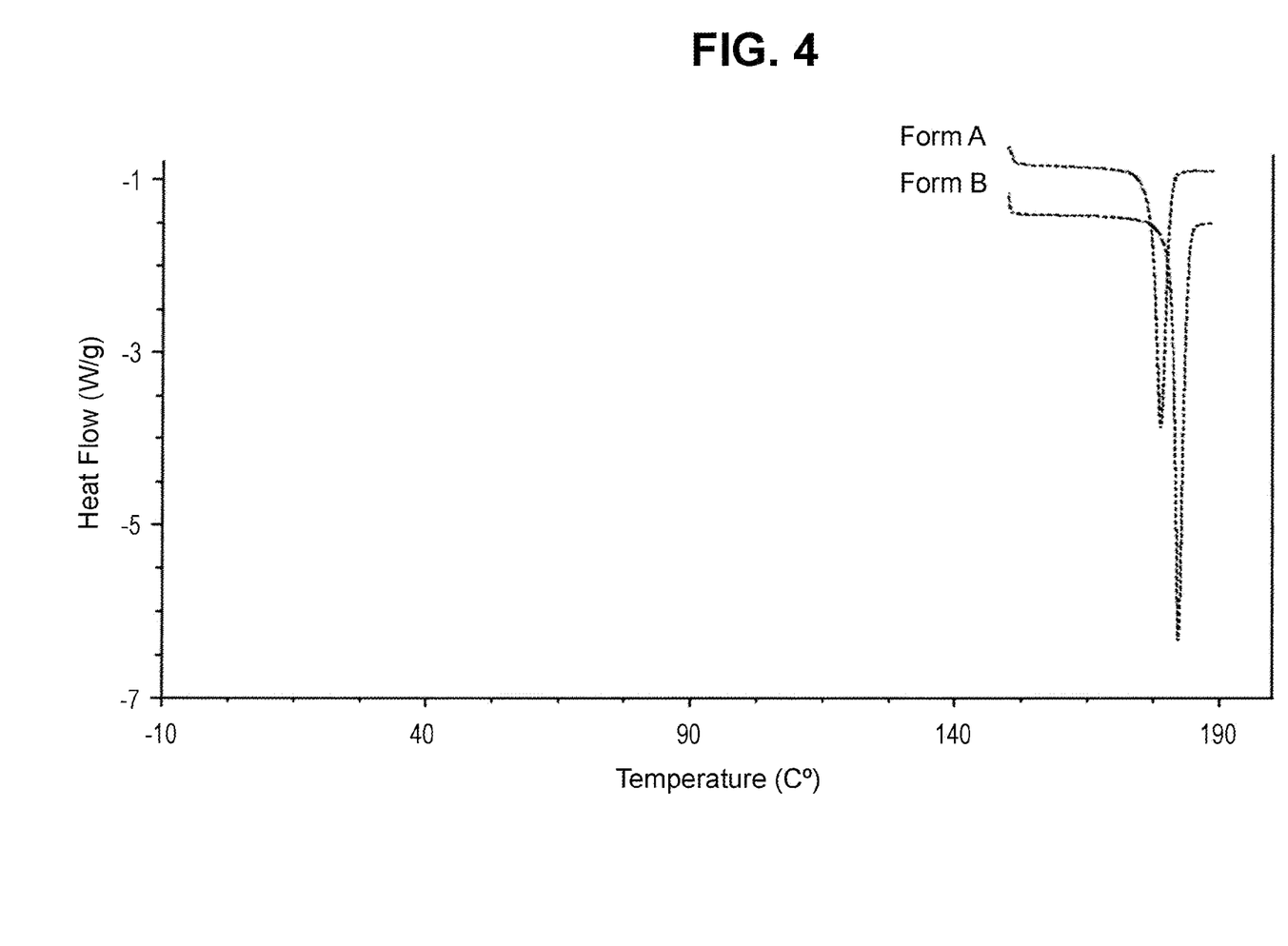
FIG. 4 shows an overlay of DSC thermograms for polymorphic Form A and Form B of bazedoxifene acetate.

Differential Scanning Calorimetry (DSC) Analysis of Polymorphic Form A and Form B of Bazedoxifene Acetate Differential scanning calorimetry (DSC) is conducted with aluminum hermetic pans, generally in the temperature interval of 150°-190° C. at 5° C./min. Form A and Form B can be distinguished by their respective melting point. The DSC results are summarized in Table 3. FIG. 2 is a DSC thermogram for polymorphic Form A of bazedoxifene acetate. FIG. 3 is a DSC thermogram for polymorphic Form B of bazedoxifene acetate. FIG. 4 shows an overlay of DSC thermograms for polymorphic Form A and Form B of bazedoxifene acetate.

TABLE 3

| Solid state | Onset (° C.)* | Peak (° C.)* | Energy (J/g)* |
|---|---|---|---|
| Form A | 176.0-177.0 | 178.0-179.0 | Endo 95-100 |
| Form B | 180.5-181.5 | 182.0-182.8 | Endo 115-120 |

*Medium values from repeated analysis on samples considered pure polymorph and on HPLC specification.

Figure 5:
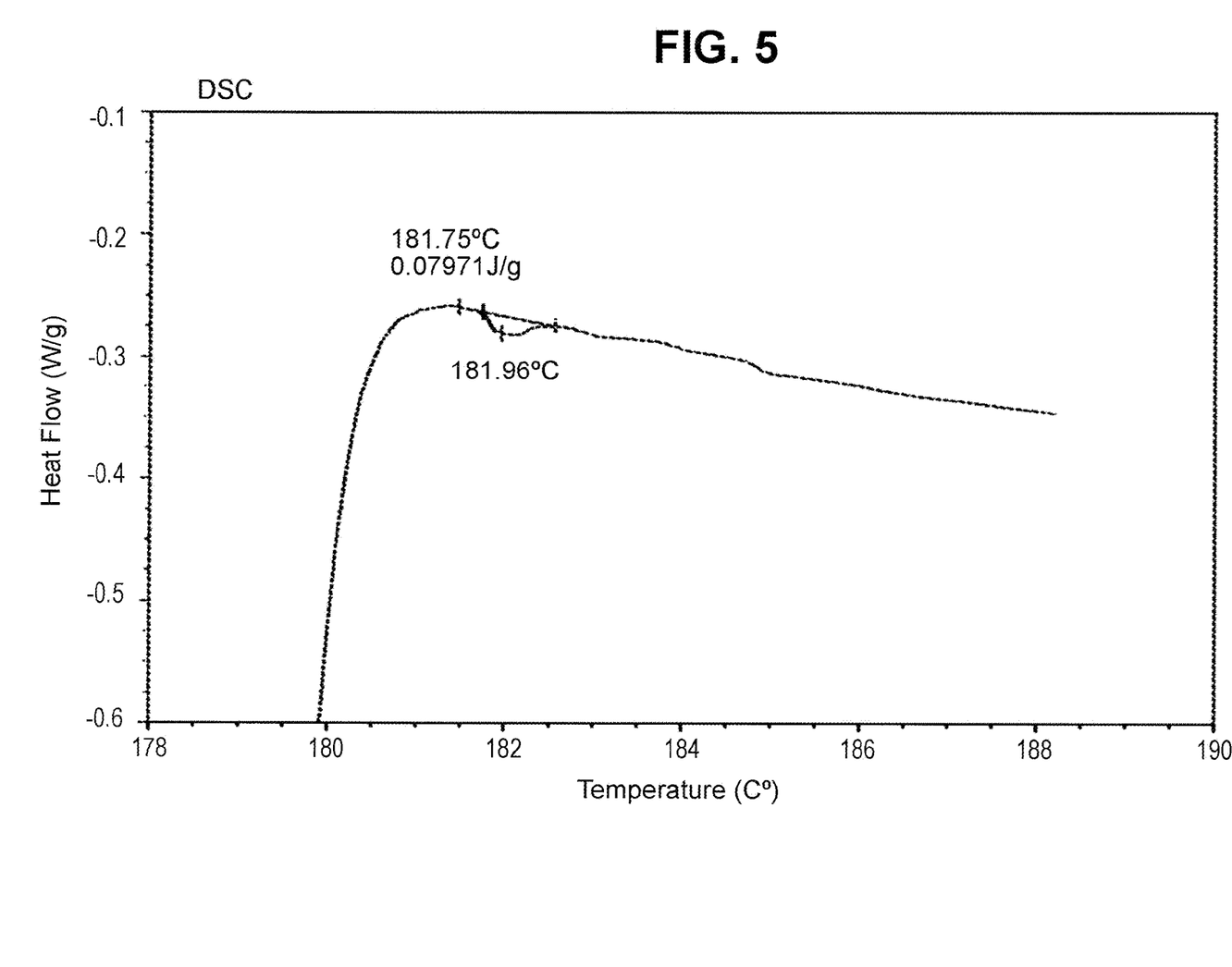
FIG. 5 is a DSC thermogram for polymorphic Form A of bazedoxifene acetate showing an example of a Form A batch with a content of Form B less than 0.1% w/w.

The DSC technique can be used to quantitatively determine the presence of polymorphic Form B of bazedoxifene acetate in batches produced as polymorphic Form A of bazedoxifene acetate. FIG. 5 shows an example of a Form A batch with a content of Form B less than 0.1% w/w.

Example 3

Figure 6:
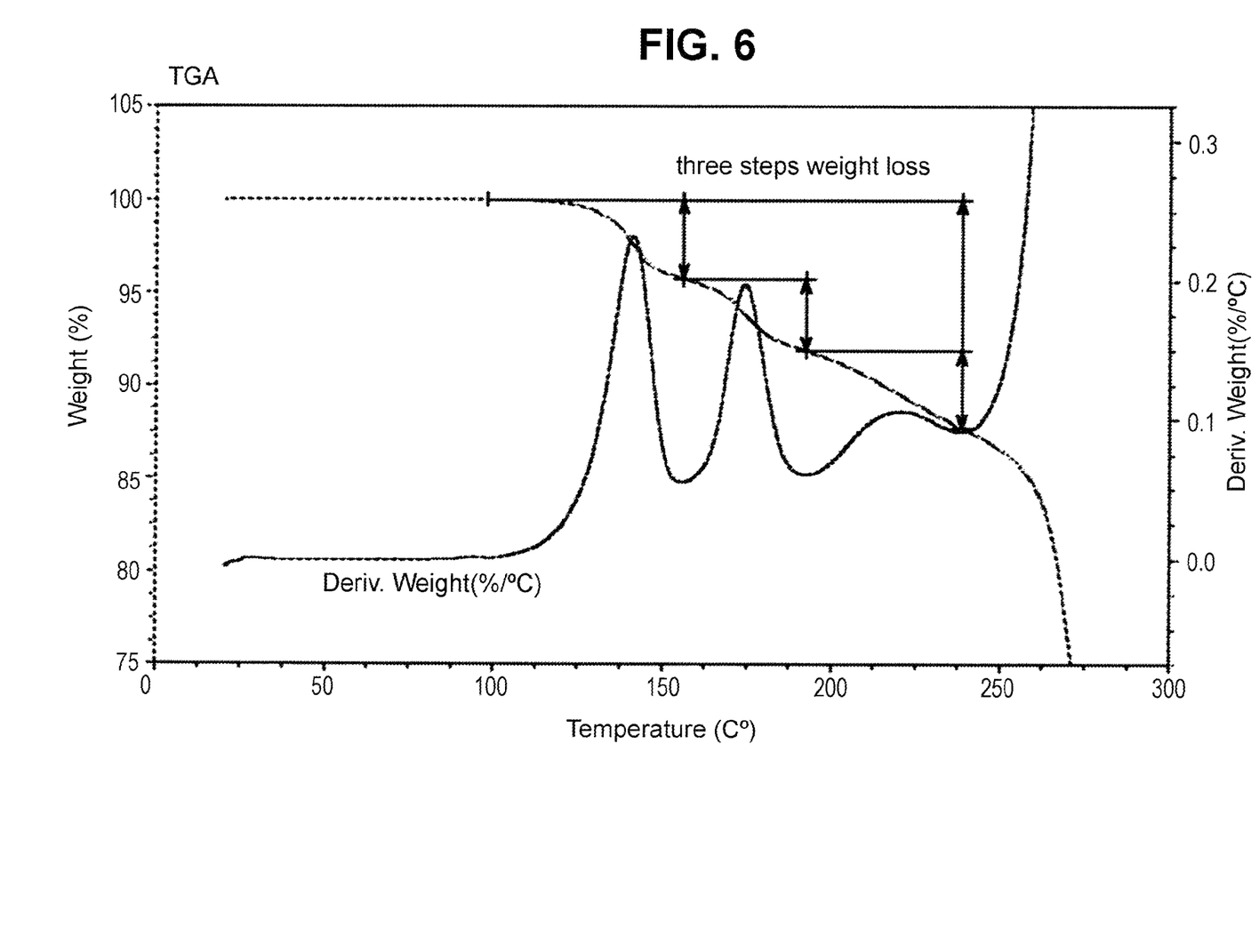
FIG. 6 shows a TGA curve for polymorphic Form A of bazedoxifene acetate.
Figure 7:
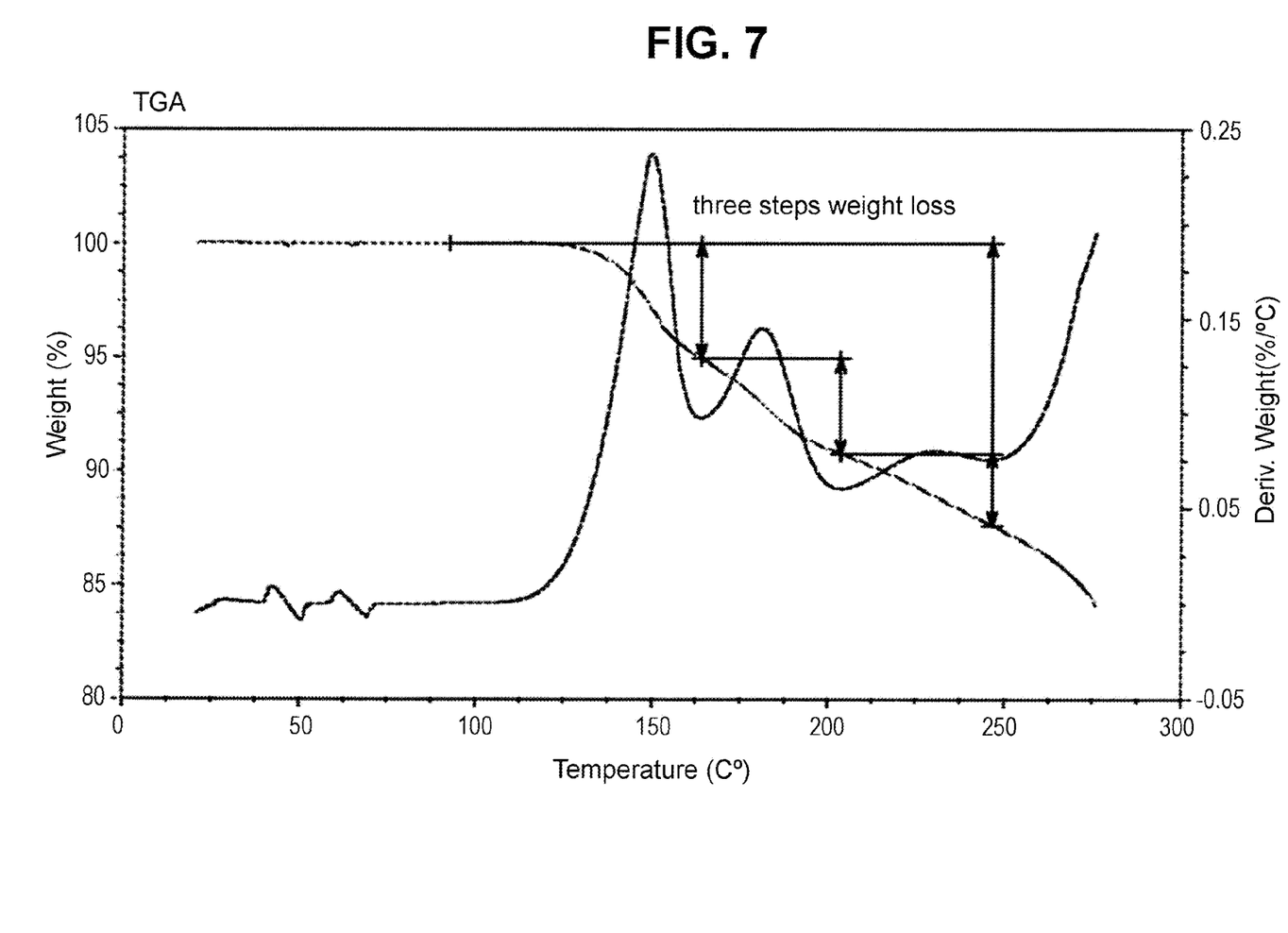
FIG. 7 shows a TGA curve for polymorphic Form B of bazedoxifene acetate.

Thermogravimetric Analysis (TGA) of Polymorphic Form A and Form B of Bazedoxifene Acetate Thermogravimetric Analysis (TGA) is conducted with a platinum pan in the temperature range of 25°-280° C. at 4° C./min. in modality "High-Res TGA". During the heating (in an open system), polymorphic Form A and Form B of bazedoxifene acetate release acetic acid above 100° C., and goes to completion generally between 235° and 245° C. The amount of the weight loss is between 11 and 12% and correspond to acetic acid of neutralization (theoretical 10.8%). The TGA profile of the acetic acid loss of Form A and Form B is subdivided into three fractions. The quantity of each fraction is characteristic of every single batch. FIG. 6 shows a TGA curve for polymorphic Form A of bazedoxifene acetate. FIG. 7 shows a TGA curve for polymorphic Form B of bazedoxifene acetate.

Example 4

Scheme 1

Preparation of Bazedoxifene Acetate

A hydrogenation vessel is charged with hexamethyleniminobenzyloxy indole (64.4 Kg), ethyl acetate (95.7 Kg, 106.3 L), ethyl alcohol (244.6 Kg, 309.7 L) and palladium/C5 (2.5% p/p, 2.54 Kg) under nitrogen. The vessel is degassed with hydrogen and then is recharged with hydrogen up to the pressure of 2 bar. The reaction mixture is heated to about 50±2° C., and the hydrogen pressure is finally set at 4 bar. After about 2 hours from the end of the hydrogen absorption, the vessel is degassed up to 0.1 bar and an HPLC analysis of the reaction mixture is performed to ensure that the reaction is complete. After a positive response of the analysis, the mixture is cooled to about 20°-30° C., and the vessel is degassed with nitrogen. Then the vessel is charged with ascorbic acid (0.50 Kg) and the internal temperature is set at about 40°-50° C. The solution is stirred at about 40°-50° C. for about 20 min.

The solution is then filtered under nitrogen through a plate filter (The plate filter is prepared as follows: Celite (2.0 Kg) is suspended in ethyl alcohol denatured with acetone/cyclohexane (a total of 60.0 Kg). The suspension is recycled with a centrifugal pump through the filter for about 30 min. The filter is maintained full of solvent, then, about 2 hours before filtering the solution, the jacket of the filter is filled with water at about 60° C.), washed with ethanol denatured cyclohexane/acetone (a total of 4.0 Kg, in two portions). Then under nitrogen glacial acetic acid (2.0 Kg) is added to the filtered solution through a charging vessel and the solution is stirred for about 20 min. and then seeded with bazedoxifene acetate Form A (0.1 Kg). The temperature of the solution is kept at about 30° C. for about 30-40 min. and then glacial acetic acid (6.9 Kg) is charged in about two hours to give a suspension.

The suspension is cooled to about 0° C. in about 1 hour, left at about 0° C. for about 2 hours, then centrifuged in two portions, and each portion is washed twice with 7.3 Kg of ethyl alcohol denatured with cyclohexane/acetone. About 55 Kg of wet product are obtained. After drying under vacuum at about 50° C., the yield was 46 Kg of bazedoxifene acetate Form A. The yield for this step is about 86-88% and the purity of the final product is about 99% or higher.

Example 5

Preparation of Bazedoxifene Acetate

Catalyst Study

It is desirable to decrease the quantity of catalyst while achieving the same or better performances, i.e. maintaining an acceptable productivity per hour, for the hydrogenation step. However, initial tests showed that it was not possible to decrease the catalyst quantity without reducing significantly the reaction rate. See, for example, Example 1 in US 2005/0227965, where the hydrogenation step therein took 20 hours. Applicants have surprisingly found that the catalyst quantity can be significantly decreased with certain types of catalyst under suitable conditions. Table 4 lists the tests in which the catalyst quantity and its concentration are modified.

TABLE 4

| Lab Experiment[a] | Solvent (ml/g hexa-methylenimino-benzyloxy indole) | Catalyst | Amount of Catalyst mol/mol hexa-methylenimino-benzyloxy indole | Reaction Time (hrs) |
|---|---|---|---|---|
| 5.1 | Ethyl acetate:Ethanol 2.25:5.25 | Pd(10%)—C dry | 0.047 | 1.5 |
| 5.2 | Ethyl acetate:Ethanol 2.35:3.30 | Pd(10%)—C dry | 0.02 | 7 |
| 5.3 | Ethyl acetate:Ethanol 2.00:3.10 | Pd(5%)—C dry | 0.02 | <5[b] |
| 5.4 | Ethyl acetate:Ethanol 1.45:2.35 | Pd(5%)—C dry | 0.01 | 2 |
| 5.5 | Ethyl acetate:Ethanol 1.45:1.90 | Pd(5%)—C dry | 0.003 | 6 |
| 5.6 | Ethyl acetate:Ethanol 1.45:1.90 | "Pearlman like" catalyst Pd(5%)—C, 50% wet | 0.003 | 1 |

[a]temperature 50° C. pressure 4 bar;
[b]The first analytical control showed complete conversion Experiment 5.6 in Table 4 shows that with a Pearlman type catalyst (non-reduced Pd), the hydrogenation time is cut down to 1 hour. Nevertheless, experiments with very low catalyst concentrations (1-3 mmol/mol hexameth­yleniminobenzyloxy indole) can cause the reaction to be very sensitive to small quantities of poisonous substances contained in the catalyst or formed during the debenzylation process. Thus, it may be desirable to use a quantity of catalyst higher than the low concentrations of 1-3 mmol/mol, for example, in an amount of 6 mmol/mol hexamethyleniminobenzyloxy indole for the hydrogenation process.

Additionally, two catalysts are compared with the catalyst amount used being equal and all the other hydrogenation conditions being the same. One catalyst is Engelhard 5% Pd on Carbon Powder catalyst code 5016 and the other is Engelhard 5% Pd on Carbon Powder DeLink code 5398. A remarkable increase of speed (more than 300%) is observed for Engelhard 5% Pd on Carbon Powder DeLink code 5398 at the same concentration.

Example 6

Preparation of Bazedoxifene Acetate

Solvent Study

Table 5 shows that the hydrogenation reaction is slow when each of toluene and ethyl acetate is used at about 26° C. (see experiments 6.2 and 6.3). The reaction time to complete the reaction is reduced when denatured ethyl alcohol is used at about 28° C. (see experiment 6.1). The denatured ethyl alcohol used includes: (a) a 95:3:5 (v/v) mixture of ethyl alcohol, cyclohexane and methyl alcohol; and (b) a 95:3:5 (v/v) mixture of ethyl alcohol, cyclohexane and acetone. No differences in reaction time are observed using these two solvent mixtures. The reaction time is reduced significantly when a mixture of AcOEt and EtOH is used at about 50° C. (see experiment 6.4).

TABLE 5

| Lab Experiment[a] | Solvent | Solvent quantity (ml)/g hexa-methyleniminobenzyloxy indole | Temperature ° C. | Reaction time (hrs) |
| --- | --- | --- | --- | --- |
| 6.1 | Denatured Ethanol | 8 | 28 | 15 |
| 6.2[b] | Toluene | 7.5 | 26 | 20 |
| 6.3[c] | AcOEt | 6.5 | 26 | 72 |
| 6.4[d] | AcOEt-EtOH | 2.25 + 5.25 | 50 | 1.5 |

[a] Catalyst Pd (10%)/C, 0.05-0.07 mol/mol hexamethyleniminobenzyloxy indole, 4 bar;
[b] 70% of unconverted raw material;
[c] 5% of unconverted raw material;
[d] 0.047 mol of Pd/mol hexamethyleniminobenzyloxy indole.

Example 7

Stability Study of Wet Polymorphic Form A of Bazedoxifene Acetate

Figure 8:
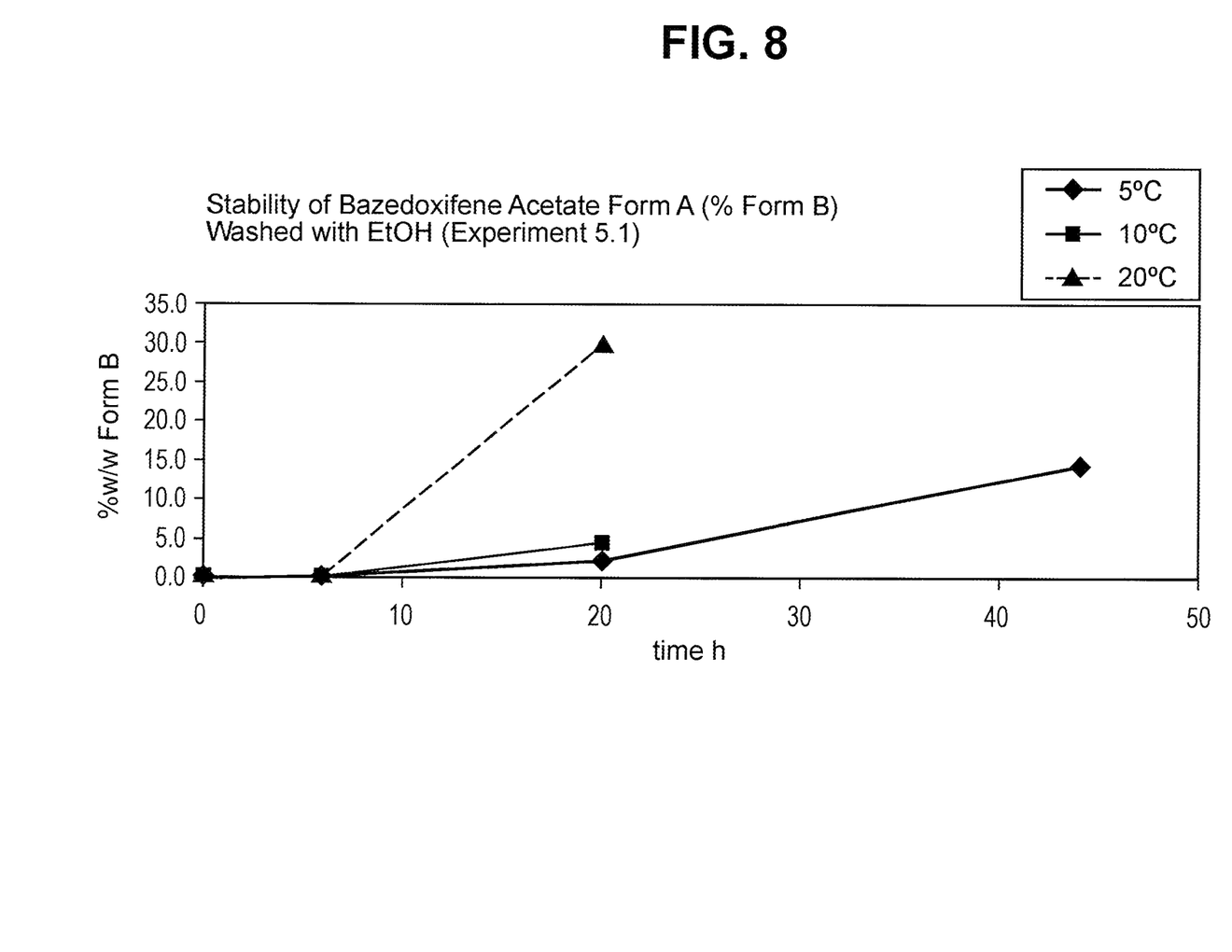
FIG. 8 shows the content of polymorphic Form B vs. time and vs. temperature for a sample of polymorphic Form A bazedoxifene acetate that is wet of EtOH.
Figure 9:
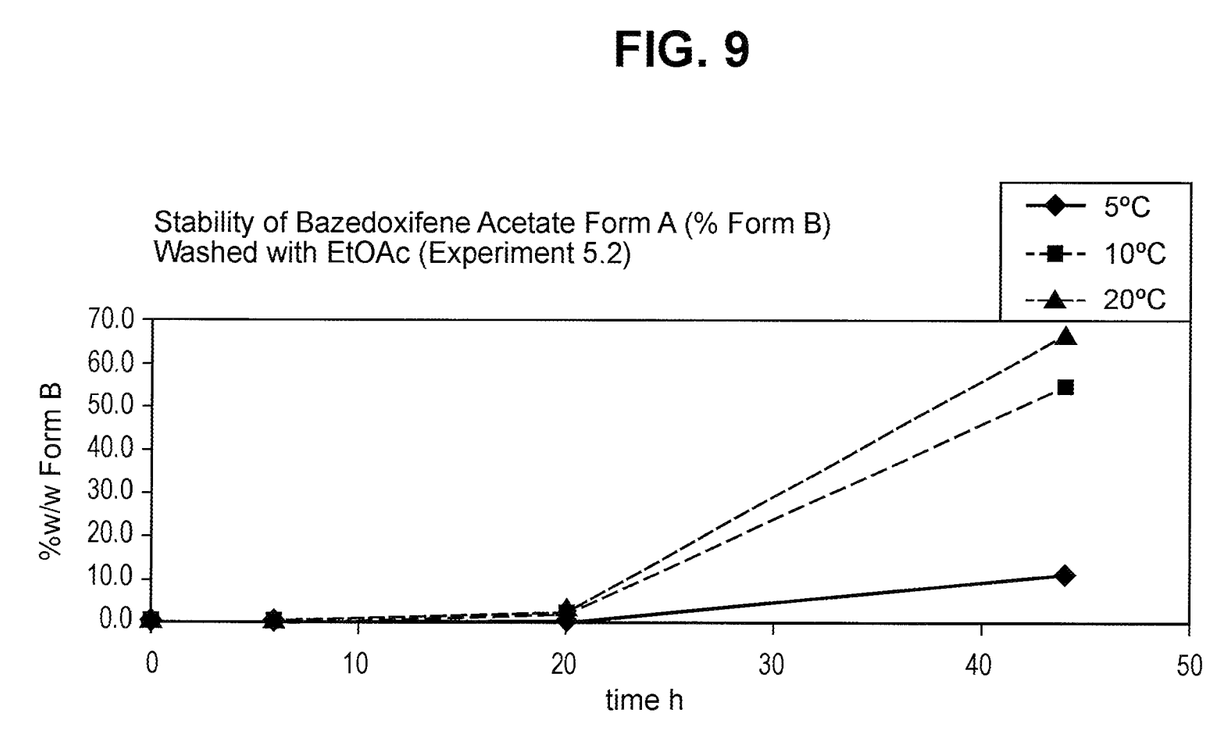
FIG. 9 shows the content of polymorphic Form B vs. time and vs. temperature for a sample of polymorphic Form A bazedoxifene acetate that is wet of EtOAc.

Example 7 shows the effect of different solvents in the transformation of wet bazedoxifene acetate Form A to Form B. A portion of the crystallization slurry of bazedoxifene acetate Form A is collected. After filtering on gooch, the wet bazedoxifene acetate Form A is divided into two portions that are washed with ethanol (experiment 7.1) and with ethyl acetate (experiment 7.2) respectively. The GC data of the solvents in the two wet products show that the product from experiment 7.1 is mainly wet of ethanol, while the product from experiment 7.2 is almost exclusively wet of ethyl acetate, and their respective Loss on Drying (LOD) is of 14.5% and 16%. Tables 6 and 7 and FIGS. 8 and 9 list the content of Form B vs. time and vs. temperature for the two samples from experiments 7.1 (wet of EtOH) and 7.2 (wet of EtOAc).

TABLE 6

Stability of Bazedoxifene Acetate Form A Wet of EtOH
% Form B batch 7.1
(LOD 14.5%)

| hrs | 5° C. | 10° C. | 20° C. |
| --- | --- | --- | --- |
| 0 | 0.0 | 0.0 | 0.0 |
| 6 | 0.0 | 0.1 | 0.4 |
| 20 | 2.5 | 4.4 | 30.0 |
| 44 | 14.5 | 68.0 | 100.0 |

TABLE 7

Stability of Bazedoxifene Acetate Form A Wet of EtOAc
% Form B batch 7.2
(LOD 16%)

| hrs | 5° C. | 10° C. | 20° C. |
| --- | --- | --- | --- |
| 0 | 0.0 | 0.0 | 0.0 |
| 6 | 0.0 | 0.0 | 0.0 |
| 20 | 0.2 | 2.0 | 2.8 |
| 44 | 10.7 | 55.2 | 66.6 |

Comparing the two cases, the transformation rate of Form A into Form B is higher for the batch washed with EtOH than that washed with EtOAc. This trend is particularly remarkable in the first 20 hours: in the same temperature conditions batch 7.1 is characterized by at least a double quantity of Form B with respect to batch 7.2. However, ethyl acetate seems only to slow down the transformation.

Example 8

Stability Study of Dry Polymorphic Form A of Bazedoxifene Acetate

Two dry samples of polymorphic form A of bazedoxifene acetate (batches that do not contain Form B), are kept at 50° C. in normal atmosphere for 50 days and no variations in the polymorph content are detected. Another dry sample of polymorphic form A of bazedoxifene acetate (that contains about 1% of Form B) is heated to 150° C. (near its melting point) and a DSC analysis of the sample does not reveal any variations in the content of Form B.

Other treatments such as industrial granulation do not appear to cause transformation of the dry product from Form A into Form B. Ten industrial batches are tested before and after granulation. Table 8 shows that there are no differences in the content of Form B in the dry samples of bazedoxifene acetate Form A.

TABLE 8

Granulation Effect on the Polymorphic Transformation of Form A of Bazedoxifene Acetate

| batch | % Form B prior to granulation | % Form B after granulation |
| --- | --- | --- |
| 8.1 | n.d | n.d. |
| 8.2 | n.d. | n.d. |
| 8.3 | n.d. | n.d. |
| 8.4 | 0.3 | 0.2 |
| 8.5 | 0.5 | 0.6 |
| 8.6 | n.d. | 0.1 |
| 8.7 | 0.3 | 0.2 |
| 8.8 | n.d. | n.d |

TABLE 8-continued

Granulation Effect on the Polymorphic Transformation
of Form A of Bazedoxifene Acetate

| batch | % Form B prior to granulation | % Form B after granulation |
|---|---|---|
| 8.9 | n.d. | n.d. |
| 8.10 | n.d. | n.d. |

We claim:

1. A method of preparing polymorphic Form A of bazedoxifene acetate, the method comprising: (a) contacting hexamethylenimino benzyloxyindole with hydrogen in a solvent comprising ethanol, and in the presence of a catalyst at elevated temperature to provide a first reaction mixture comprising bazedoxifene free base, wherein the first reaction mixture is substantially free from hexamethylenimino benzyloxyindole, wherein step (a) is completed in less than about 10 hours; (b) treating said first reaction mixture with an antioxidant to provide a second reaction mixture; (c) filtering said second reaction mixture to provide a solution comprising bazedoxifene free base; and (d) treating said solution with acetic acid to crystallize polymorphic Form A of bazedoxifene acetate.

2. The method of claim 1, wherein in step (a), the solvent further comprises at least one solvent selected from the group consisting of ethyl acetate, acetone, cyclohexane and methanol.

3. The method of claim 1, wherein step (a) is completed in less than about 4 hours.

4. The method of claim 1, wherein in step (a), the catalyst is a Pd/C catalyst.

5. The method claim 4, wherein the Pd/C catalyst used is in an amount (a) less than about 10 mmol per mmol of hexamethylenimino benzyloxyindole used.

6. The method of claim 4, wherein the Pd/C catalyst has a total surface area (B.E.T) of more than about 1100 $m^2$/g.

7. The method of claim 4, wherein the Pd/C catalyst is non-reduced Pd on moist carbon.

8. The method of claim 1, wherein step (a) is carried out at a temperature of about 30° C. or higher.

9. The method of claim 1, wherein step (a) is carried out at a temperature of about 50° C.

10. The method of claim 1, wherein in step (b), said antioxidant is selected from ascorbic acid, sodium ascorbate, ascorbyl palmitate, citric acid, propyl gallate, alpha Tocopherol (vitamin E), vitamin E TPGS, vitamin E acetate, butylated hydroxytoluene, butylated hydroxyanisole and mixtures thereof.

11. The method of claim 1, wherein in step (b), said antioxidant is ascorbic acid.

12. The method of claim 1, wherein step (d) is facilitated by seeding with polymorphic Form A of bazedoxifene acetate.

13. The method of claim 1, wherein step (d) is carried out at a temperature of about 40° C. or lower.

14. The method of claim 1, wherein step (d) is carried out at a temperature ranging from about 20° C. to about 35° C.

15. The method of claim 1, wherein in step (d said polymorphic Form A of bazedoxifene acetate is more than 99% pure.

16. The method of claim 1, further comprising isolating polymorphic Form A of bazedoxifene acetate by filtration, washing and drying.

17. The method of claim 16, wherein said drying is conducted in an agitated filter dryer or a tumble dryer.

* * * * *